United States Patent [19]

Frohardt

[11] Patent Number: 4,945,253
[45] Date of Patent: Jul. 31, 1990

[54] MEANS OF ENHANCING THE SENSITIVITY OF A GLOSS SENSOR

[75] Inventor: Allen Frohardt, San Jose, Calif.

[73] Assignee: Measurex Corporation, Cupertino, Calif.

[21] Appl. No.: 282,102

[22] Filed: Dec. 9, 1988

[51] Int. Cl.$^5$ .............................................. G01N 21/86
[52] U.S. Cl. ..................................... 250/571; 356/446
[58] Field of Search ....................... 356/446, 447, 448; 250/571, 572, 216; 350/314

[56] References Cited

U.S. PATENT DOCUMENTS

| | | | |
|---|---|---|---|
| 195,054 | 4/1963 | Cattaro et al. | D52/6 |
| 1,988,556 | 1/1935 | Hunter | 88/14 |
| 2,063,551 | 12/1936 | Hunter | 88/14 |
| 2,127,447 | 8/1938 | Carpenter et al. | 88/14 |
| 2,471,750 | 5/1949 | Hunter | 250/41.5 |
| 2,546,450 | 3/1951 | Hunter | 88/14 |
| 2,739,246 | 3/1956 | Hunter | 250/220 |
| 3,229,564 | 1/1966 | Meltzer | 356/446 |
| 3,549,264 | 12/1970 | Christie | 356/210 |
| 3,669,540 | 6/1972 | Rattman et al. | 350/314 |
| 3,693,025 | 9/1972 | Brunton | 250/83.3 |
| 3,700,314 | 10/1972 | Busby | 350/314 |
| 3,890,049 | 6/1975 | Collins et al. | 356/199 |
| 4,072,426 | 2/1978 | Horn | 356/446 |
| 4,412,746 | 11/1983 | Yokouchi | 356/446 |
| 4,583,861 | 4/1986 | Yamaji et al. | 356/446 |
| 4,613,235 | 9/1986 | Suga | 356/446 |
| 4,770,536 | 9/1988 | Golberstein | 356/446 |

OTHER PUBLICATIONS

"New Gloss Tests of Paper Products", by Richard S. Hunter, TAPPI, Jan. 1955, vol. 38, No. 1, pp. 17-24.

Primary Examiner—David C. Nelms
Attorney, Agent, or Firm—Spensley Horn Jubas & Lubitz

[57] ABSTRACT

A gloss sensor for optically measuring the gloss or reflectance of a surface. The gloss sensor includes a light source of emitting a light beam toward a surface to be measured. The gloss sensor also includes a light detecting device arranged to preferentially detect the intensity of the diffusely reflected component of the reflected light beam relative to the specularly reflected component.

21 Claims, 1 Drawing Sheet

MEANS OF ENHANCING THE SENSITIVITY OF A GLOSS SENSOR

BACKGROUND OF THE INVENTION

The present invention relates to a method and device for optically measuring the gloss or reflectance of a surface, and more particularly, to a gloss sensor having increased sensitivity to changes in the gloss of a surface and to a method for increasing the sensitivity of gloss sensors.

One of the parameters used in determining the quality of a particular surface is the gloss of the surface. For example, in the papermaking industry, various grades of paper having different surface gloss qualities are produced to suit various applications. During the production of paper sheet, it is often desirable to continuously or periodically measure the gloss of the surface of the sheet to ensure that the surface of the sheet being produced has the desired gloss. Typically, the gloss of paper is measured with a gloss sensor during the last step of paper production just before the produced sheet is packaged in the form of rolls.

Known devices for determining the gloss of surfaces include, for example, an optical system which measures the intensity of a beam of light reflected from the surface under test. Typically, the gloss of such a surface is determined by comparing its total reflectance (specular and diffuse) to the reflectance of a gloss standard, such as, for example, a glass tile having a polished surface of a known gloss. "Specular reflectance" refers to reflections of the type produced from a polished, perfectly flat surface or mirror. "Diffuse reflectance", on the other hand, refers to scattered reflections produced by irregular surfaces. Because no actual surface is perfectly specularly reflective, reflections from any real surface will have both a specular component and a diffuse component.

Specifically, in measuring the reflectance of a surface, an incident beam of light is first projected onto the surface from a light source and a resulting reflected beam, having both specular and diffuse reflection components, is reflected from the surface. A light intensity detector is positioned to receive the reflected beam and measure its intensity. To determine the gloss of the surface, the intensity of the reflected beam is compared with a known intensity value, such as the intensity of a reflected beam which results when the incident beam from the light source is reflected from a polished glass tile having a known gloss. This comparison can be accomplished with known electronic devices.

Typically, a gloss sensor viewing angle is fixed. That is, the angle which the incident and reflected beams make with the normal to the surface plane remains constant during the reflectance measurement of that surface. Different angles, with respect to the normal to the surface plane, are used for different sheet reflectivity measurements, with smaller angles being employed for more reflective surfaces. For reflectance measurements of paper, the standard angles, with respect to the normal to the plane of the paper, are 20° for paper having a high reflectivity surface and 75° for paper with a low reflectivity surface.

SUMMARY OF THE INVENTION

The present invention is directed to a gloss sensor having a relatively high sensitivity to changes in the gloss of a surface being examined by the sensor. The invention includes a gloss sensor having a reflected light intensity detector constructed such that the detector is preferentially sensitive to diffuse reflection from the surface, as opposed to specular reflection from the surface.

In one embodiment of the present invention, preferential sensitivity to diffuse reflection is obtained by placing the light intensity detector in the path of the reflected beam and then positioning a light attenuating device, such as a filter, in the path of the reflected beam between the surface and intensity detector. The light attenuating device is disposed such that it preferentially attenuates only the central portion of the reflected beam containing the specularly reflected light. The diffusely reflected light toward the outer edges of the reflected beam is allowed to pass by the attenuating device, and falls, essentially unattenuated, upon the intensity detector.

By the attenuation of the relatively intense specular reflection, the intensity detector of the gloss sensor exhibits an increase in sensitivity to changes in the intensity of the relatively less intense diffuse reflection. That is, the change in the detected intensity of reflected light is proportionately greater, for a given change in gloss, when the detected reflection is primarily the relatively low intensity diffuse reflection rather than an overall measurement of reflection intensity resulting from an unbiased combination of the diffuse reflection and the relatively high intensity specular reflection. The above construction thereby affects an increase in the overall sensitivity of the gloss sensor to changes in the gloss of the surface being examined.

BRIEF DESCRIPTION OF THE DRAWINGS

The following detailed description of the invention will be made with reference to the accompanying figures, wherein like numerals designate corresponding parts in the several figures.

DETAILED DESCRIPTION OF THE PREFERRED EMBODIMENTS

The following description is of the best presently contemplated mode of carrying out the invention. This description is made for the purpose of illustrating the general principles of the invention and should not be taken in a limiting sense. The scope of the invention should be determined by reference to the accompanying claims.

Figure 1:
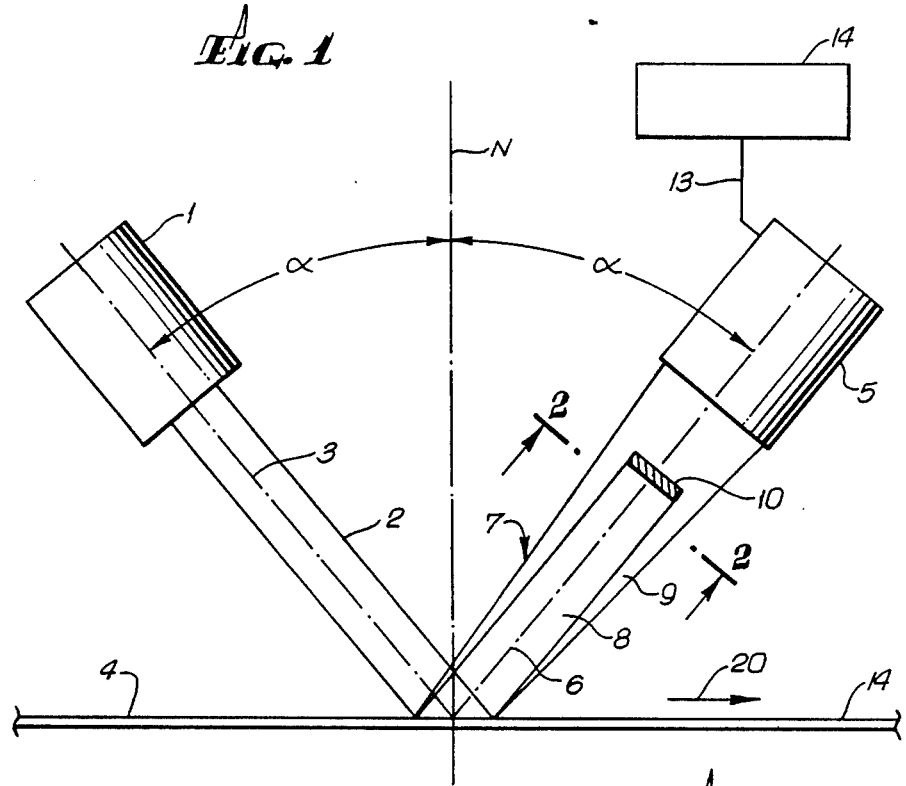
FIG. 1 is a schematic side view of an apparatus according one embodiment of the present invention.

Refering to FIG. 1, a light source 1 is shown emitting a beam of light 2 along an optical axis 3. The light source 1 may comprise, for example, a tungsten halogen lamp, or any other suitable means for emitting light. Also shown in FIG. 1 is a light intensity detector 5. This light detector 5 may comprise, for example, a photodiode, or any other suitable means for detecting light and producing a signal indicative of the intensity of the detected light. The light source 1 and the light intensity detector 5 comprise elements of a fixed angle gloss sensor (having fixed angles $\alpha$) which may be used to measure the gloss of a continuous paper sheet 14 being manufactured by a papermaking machine (not shown) in a paper mill. In FIG. 1 the paper sheet 14 is moving in the direction of arrow 20.

The light detector 5 is operatively connected along line 13 to a circuit 14, which may include a suitably programmed computer. The circuit 14 receives the signal from the light detector 5, evaluates the signal by comparing the intensity of the signal to the intensity of a signal which would be received from a known gloss standard, and then provides an output indicative of the gloss of the paper surface 4 then being evaluated. In certain situations, the circuit 14 may include a process control computer which can control the process producing the paper sheet so as to obtain a desired sheet gloss. Circuits and devices for performing the functions of evaluating signal intensities and controlling the sheet gloss are known in the paper manufacturing industry and, therefore, in an effort to simplify the present disclosure, will not be described in further detail herein.

The light source 1 and the light detector 5 are arranged to be at equal angles $\alpha$ with respect to the normal N to the surface 4. That is, the light source 1 is arranged such that the optical axis 3 thereof forms an angle $\alpha$ with the normal N, while the light detector 5 is arranged such that the optical axis 6 thereof also forms the same angle $\alpha$ with the normal N. Furthermore, the optical axis 3 of the light source 1 and the optical axis 6 of the light detector 5 are positioned in a common plane with the normal N to the surface 4. In this manner, a light beam 2 emitted from the light source 1 is reflected from the surface 4 and received by the light detector 5.

The emitted beam 2 upon reflection from the surface 4, forms a reflected beam 7. Due to the above described arrangement of the light source 1 and the light detector 5, the incident beam 2, projected along the optical axis 3, is reflected from the surface 4 and forms a reflected beam 7 along the optical axis 6. As shown in FIG. 1, the reflected beam 7 is composed of a central specularly reflected beam component 8 and an outer diffusely reflected beam component 9, both of which share the common optical axis 6.

In the embodiment of FIG. 1, a light attenuating device 10 is arranged between the surface 4 and the light detector 5. The light attenuating device 10 is arranged to be substantially centered with respect to the optical axis 6. In this way, part or all of the central specularly reflected beam 8 can be attenuated before encountering the light detector 5. In the FIG. 1 embodiment, the light attenuating device 10 is shaped and arranged only to attenuate the specularly reflected central beam 8. In this regard, the diffusely reflected outer beam 9 is received substantially unattenuated by the light detector 5, while the specularly reflected beam 8 is attenuated before reaching the light detector 5.

The light attenuating device 10 may comprise an opaque member which completely blocks light, or may comprise a partially opaque member which blocks only a portion of the light passing therethrough. Other embodiments of the light attenuating device 10 will be described below.

In operation, the gloss sensor which employs the light source 1 and the light detector 5 of FIG. 1 operates in a somewhat similar manner to the known devices described above. However, to the best of applicant's knowledge, the inclusion of the light attentuating device 10, according to the above-described embodiment, is completely unknown in the prior art. The inclusion of this light attenuating device provides a greater sensitivity to changes in the gloss of a surface than that which is provided by previously known gloss sensors.

According to the above-described embodiment, the light attenuating device 10 operates to attenuate the generally stronger (more intense) specularly reflected beam 8, while allowing the generally weaker (less intense) diffusely reflected beam 9 to pass substantially unattenuated to the light detector 5. In this regard, the high intensity specular reflections can be completely removed or at least partially attenuated from the light beam 7 received by the light detector 5. The light detector will, thereby, provide readings only, or preferentially, of the intensity of the diffusely reflected beam 9, and will not provide the high intensity readings characteristic of specular reflections. By employing means for attenuating the relatively intense specular reflections, the gloss sensor will exhibit an increase in sensitivity to changes in the diffusely reflected beam 9 and, thus, to changes in the gloss of the surface 4. The present invention is particularly useful for measuring the gloss of high gloss paper sheets at relatively large angles (e.g., $\alpha \geq 75°$) with respect to the normal to the sheet.

Figure 2:
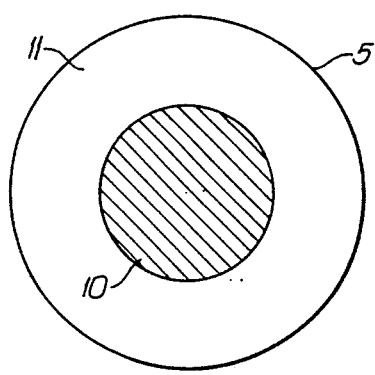
FIG. 2 is a view of a light intensity detector and an attenuating device, taken along line 2—2 in FIG. 1 perpendicular to the optical axis of the light intensity detector.

FIG. 2 is a view of the light attenuating device 10 and the light detector 5 along the optical axis 6. As shown in the FIG. 2 embodiment, the light attenuating device 10 is substantially centered with respect to the optical axis 6 and the light detector 5. In this manner, only an outer annular portion 11 of the light detector 5 is left exposed to unattenuated diffusely reflected light. As described above, the light attenuating device 10 is shaped and positioned so as to attenuate only the central specular reflections, while allowing diffuse reflections to pass and impinge substantially unattenuated on the annular portion 11 of the light detector 5.

The light attenuating device 10 shown in FIG. 2 is hatched to indicated that it is opaque and thus blocks all of the light impinging thereon. However, it is within the scope of the present invention to provide a light attenuating device 10 which blocks only a portion of the light impinging thereon.

Figure 3:
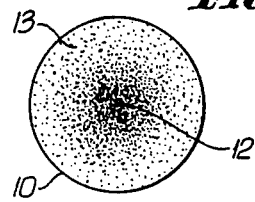
FIG. 3 illustrates an attenuating device which, according to an alternative embodiment of the present invention, may be placed in the path of the reflected beam.

FIG. 3 shows another embodiment of the light attenuating device 10. In this embodiment, the light attenuating device 10 comprises a graded optical density filter. The graded optical density filter of FIG. 3 blocks only a portion of the light impinging thereon, while allowing a portion of the light to pass therethrough. The graded optical density filter has a greater concentration of filter elements (e.g., opaque dye or paint) toward the central region 12 than toward the outer region 13. Thus, the central region 12 blocks a greater portion of light impinging thereon than does outer region 13. The high intensity specular reflections impinging upon the central region 12 are blocked to a greater extent than the diffuse reflections impinging on the outer region 13.

The graded optical density filter of FIG. 3 may be disposed in the path of the reflected beam as shown in FIG. 1. Alternatively, the graded optical density filter may be arranged so as to completely cover the light receiving portion of the light detector 5. In this embodiment, all of the light received by the light detector 5 will pass through the graded optical density filter. However, the light impinging on the central portion 12 of the filter 10 will be attenuated to a greater extent than the light impinging on the outer region 13 of the filter 10. Thus, the specular reflection component 8 of the reflected beam 7 will be attenuated to a greater extent than the diffusely reflected component 9 of the reflected beam 7.

While the above-described embodiments provide a light attenuating device 10 as a separate element with respect to the light detector 5, it is also within the scope of the present invention to incorporate the light attenuating device 10 on or within the light detector 5 itself. Thus, the light attenuating device 10 may include a completely or partially opaque dark spot (e.g., dye or paint) centrally located on the light receiving portion of the detector 5.

Figure 4:
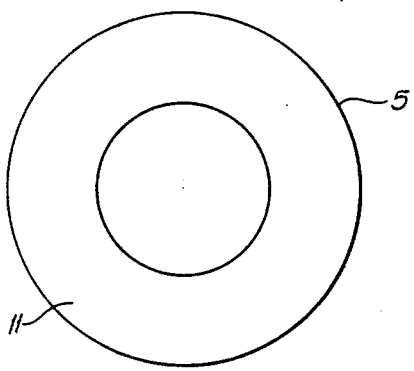
FIG. 4 illustrates the light receiving device having a ring shaped detector, which preferentially receives diffuse reflections.

In yet another embodiment shown in FIG. 4, the light receiving device 10, 5 may comprise a photosensitive device, such as a photodiode, photodiodes, a photoresistive element or, plural photoresistive elements, shaped or arranged in a ring 11 so as to receive substantially only the diffuse reflections.

While several presently preferred embodiments of the present invention have been described, it will be understood that various modifications may be made without departing from the spirit and scope of the invention. Furthermore, although the present invention has been described with reference to the gloss measurement of paper, the present invention is also suitable for measuring the gloss of surfaces other than paper. Accordingly, it is understood that the invention is not limited by the specific illustrated embodiments, but only by the scope of the appended claims and equivents thereof.

What is claimed is:

1. A gloss sensor for determining the gloss of a surface, comprising:

a light source for emitting an incident light beam onto the surface, the source having an optical axis forming an angle, not equal to zero, with respect to a normal to the surface, thereby causing a light beam to be reflected from the surface, the reflected light beam having a specularly reflected component and a diffusely reflected component;

a light detector positioned to detect the reflected light beam including the diffusely reflected component falling beyond the outer edge of the specularly reflected component; and light attenuating means, disposed in the path of the reflected beam at a point before the reflected beam reaches the light detector, for preferentially attenuating at least a portion of the specularly reflected component relative to the diffusely reflected component.

2. A gloss sensor as claimed in claim 1, wherein the light detector produces an output signal indicative of the intensity of the detected light and the sensor further includes a comparison means operatively coupled to the light detector for comparing the intensity of the light detected by the light detector with a predetermined value, and for producing an output signal, based upon the comparison, indicative of the gloss of the surface.

3. A gloss sensor as claimed in claim 1, wherein the light attenuating means comprises an opaque member disposed between the surface and the light detector in the path of the specularly reflected component of the reflected beam.

4. A gloss sensor as claimed in claim 1, wherein the light attentuating means comprises a graded optical density filter disposed between the surface and the light detector in the path of the reflected beam, the graded optical density filter being such as to preferentially attenuate the specularly reflected component relative to the diffusely reflected component.

5. A gloss sensor for determining the gloss of a surface, comprising:

a light source for emitting an incident light beam onto the surface, the source having an optical axis forming an angle, not equal to zero, with respect to a normal to the surface, thereby causing a light beam to be reflected from the surface, the reflected light beam having a specularly reflected component and a diffusely reflected component; and a light detector having a light detecting surface for detecting the reflected light beam, the light detecting surface being shaped to preferentially be impinged by at least a portion of the diffusely reflected component of the reflected beam as opposed to the specularly reflected component of the reflected beam, the detected reflected light beam being indicative of the gloss of the surface.

6. A gloss sensor as claimed in claim 5, wherein the light detecting surface of the light detector is ring shaped.

7. A method for measuring the gloss of a surface, said method comprising the steps of:

emitting an incident beam of light along an optical axis forming an angle, not equal to zero, with respect to a normal to the surface, onto the surface so as to cause a reflected beam of light to be reflected from the surface, the reflected beam having a specularly reflected component and a diffusely reflected component;

preferentially attenuating the specularly reflected component relative to the diffusely reflected component;

detecting the intensity of at least a portion of the diffusely reflected component falling beyond the outer edge of the specularly reflected component after the specularly reflected component has been attenuated; and determining the gloss of the surface based upon the detected intensity and a predetermined intensity value.

8. A method for measuring the gloss of a surface, the method comprising the steps of:

emitting an incident beam of light along an optical axis forming an angle, not equal to zero, with respect to a normal to the surface, onto the surface so as to cause a reflected beam of light to be reflected from the surface, the reflected beam having a specularly reflected component and a diffusely reflected component;

preferentially detecting the intensity of the diffusely reflected component relative to the specularly reflected component; and determining the gloss of the surface based upon the preferentially detected intensity and a predetermined intensity value.

9. A gloss sensor as in claim 1, wherein the light attenuating means comprises a graded optical density filter for blocking a portion of light impinging thereon, the filter comprising a member having a center region and a peripheral region, and filter means for blocking a greater amount of light impinging on the center region than on the peripheral region.

10. A graded optical density filter as in claim 9, wherein the member includes relatively optically clear material, and the filter means includes opaque material associated with the member having a concentration which gradually diminishes from the center region toward the peripheral region.

11. A graded optical density filter as in claim 10, wherein said member is substantially disk shaped.

12. A gloss sensor for determining the gloss of a surface, comprising:
 a light source for emitting an incident light beam onto the surface, the source having an optical axis forming an angle, not equal to zero, with respect to a normal to the surface, thereby causing a light beam to be reflected from the surface, the reflected light beam having a specularly reflected component and a diffusely reflected component; and
 a light detector having a light detecting surface for detecting the reflected light beam, wherein the detector is operable to generate a signal indicative of the intensity of the detected light, the light detecting surface being disposed to preferentially be impinged by at least a portion of the diffusely reflected component of the reflected beam falling beyond the outer edge of the specularly reflected component as opposed to the specularly reflected component of the reflected beam; and
 a comparison means, operatively coupled to the light detector, for comparing the value of the signal with a predetermined value and producing an output, based upon the comparison, indicative of the gloss of the surface.

13. A method for measuring the gloss of a moving surface, the method comprising the steps of:
 emitting an incident beam of light along an optical axis forming an angle, not equal to zero, with respect to a normal to the surface, onto the moving surface so as to cause a reflected beam of light to be reflected from the moving surface, the reflected beam having a specularly reflected component and a diffusely reflected component;
 preferentially attenuating the specularly reflected component relative to the diffusely reflected component; and
 detecting the intensity of at least a portion of the reflected beam, including the diffusely reflected component falling beyond the outer edge of the specularly reflected component after the specularly reflected component has been attenuated.

14. A gloss sensor as claim in claim 1, wherein the light source is operable to emit the incident light beam onto a moving surface.

15. A gloss sensor as claimed in claim 14, wherein the light detector is operable to produce a first signal indicative of the intensity of the detected light and the sensor further includes a comparison means, operatively coupled to the light detector, for receiving the first signal and comparing the intensity of the light detected by the light detector with a predetermined value, and for producing a second signal, based upon the comparison, indicative of the gloss of the surface.

16. A gloss sensor as claimed in claim 1, wherein the specularly reflected component defines a line and the light detector is positioned along the line.

17. A gloss sensor as claimed in claim 16, wherein the light detector is operable to produce a first signal indicative of the intensity of the detected light and the sensor further includes a comparison means, operatively coupled to the light detector, for receiving the first signal and comparing the intensity of the light detected by the light detector with a predetermined value, and for producing a second signal, based upon the comparison, indicative of the gloss of the surface.

18. A gloss sensor as claimed in claim 5, wherein the light detector is operable to produce a first signal indicative of the intensity of the detected light and the sensor further includes a comparison means, operatively coupled to the light detector, for receiving the first signal and comparing the intensity of the light detected by the light detector with a predetermined value, and for producing a second signal, based upon the comparison, indicative of the gloss of the surface.

19. A gloss sensor as claimed in claim 6, wherein the light detector is operable to produce a first signal indicative of the intensity of the detected light and the sensor further includes a comparison means, operatively coupled to the light detector, for receiving the first signal and comparing the intensity of the light detected by the light detector with a predetermined value, and for producing a second signal, based upon the comparison, indicative of the gloss of the surface.

20. A method as claimed in claim 7, wherein the incident light beam is emitted onto a moving surface.

21. A method as claimed in claim 8, wherein the incident light beam is emitted onto a moving surface.

* * * * *